United States Patent [19]
De Luca et al.

[11] Patent Number: 5,388,591
[45] Date of Patent: Feb. 14, 1995

[54] METHOD AND APPARATUS FOR ANALYZING THE HUMAN POSTURAL CONTROL SYSTEM

[75] Inventors: Carlo J. De Luca, Wellesley Hills; James J. Collins, Brighton, both of Mass.

[73] Assignee: Trustees of Boston University, Boston, Mass.

[21] Appl. No.: 987,715

[22] Filed: Dec. 9, 1992

[51] Int. Cl.$^6$ .............................................. A61B 5/103
[52] U.S. Cl. .................................................... 128/779
[58] Field of Search ......................... 128/774, 779, 782

[56] References Cited

U.S. PATENT DOCUMENTS

| | | | |
|---|---|---|---|
| 3,712,294 | 1/1973 | Muller | 128/782 |
| 3,826,145 | 7/1974 | McFarland | 128/782 |
| 4,598,717 | 7/1986 | Pedotti | 128/779 |

OTHER PUBLICATIONS

Ghosh et al. "Preliminary Study on . . . Extremity Disability" Med & Biol. Eng & Comput. 1979 737–741.
Terekhou "Measuring Man's Stability of Stance" Jn. of Clinical Eng. Jan./Mar. 1979 pp. 61–65.

*Primary Examiner*—Max Hindenburg
*Attorney, Agent, or Firm*—Baker & Botts

[57] ABSTRACT

A method and an apparatus for analyzing the human postural control system includes computing the mean square displacement of the center of pressure beneath a subject's feet vs. the time interval. The result is plotted as a stabilogram diffusion plot. The stabilogram diffusion plot, since reproducible, provides physiologically meaningful information from which an assessment of the subject's postural control system can be made. A Brownian diffusion coefficient, which is indicative of the level of stochastic activity of the center of pressure, can be calculated from the slope of the stabilogram diffusion plot. Also, from the slope of the log-log stabilogram diffusion plot, a determination can be made as to whether the system is moving closer to or away from a state of relative equilibrium. Finally, a short term open-loop postural control scheme, which operates before a long term closed-loop feedback postural control scheme activates, can be studied from the stabilogram diffusion plot. Also, from the stabilogram diffusion plot, a determination can be made as to when the postural control system switches from open-loop control to closed-loop control.

39 Claims, 4 Drawing Sheets

METHOD AND APPARATUS FOR ANALYZING THE HUMAN POSTURAL CONTROL SYSTEM

BACKGROUND OF THE INVENTION

1. Field of the Invention

This invention relates to a method and an apparatus for collecting and analyzing data, and more particularly, for collecting and analyzing data pertaining to the center of pressure beneath a standing subject's feet as an upright posture is maintained.

2. Background of the Prior Art

The task of maintaining an upright posture involves a complex sensorimotor system. Even when a young, healthy individual attempts to stand still, the center of gravity of his or her body and the center of pressure under his or her feet move relative to a global coordinate system.

A plot of the time-varying coordinates of the center of pressure beneath the feet of a standing subject is known as a stabilogram. One such stabilogram is shown in FIG. 1. By studying signatures of the center of pressure, researchers have attempted to correlate the center of pressure with the dynamics of the neuromuscular postural control system working to maintain human balance.

For example, a number of biomechanical researchers have attempted to evaluate postural sway by using a force platform to measure the anteroposterior and mediolateral displacements of the center of pressure over the plane of support. Other researchers have limited the analysis of center of pressure trajectories to summary statistics, e.g., the calculation of the length of the sway path, average radial area. In either case, the data obtained in prior static posturography have been limited by the lack of a reliable, consistently useful method for extracting repeatable, physiologically meaningful information from stabilograms. In other words, since the signature of the center of pressure will not repeat itself even when tests of the same subject are taken immediately after one another, it has been difficult to interpret the data obtained from the center of pressure signatures.

Within the neuromuscular postural control system there are known closed-loop feedback systems. The closed-loop feedback systems synthesize information from visual, vestibular, and somatosensory receptors. During any given task, the human postural control system receives information from these receptors, and depending upon the information received, corrective postural control signals are sent to the neuromuscular system. The corrective postural control signals from the visual, vestibular, and somatosensory systems are analogous to a closed-loop feedback control system. It has generally been thought that these afferent signals (visual, vestibular and somatosensory) were the exclusive regulators of the musculature during quiet standing. However, traditional clinical results have overlooked possible short term open-loop control schemes operating on the postural control system before the long term closed-loop system activates.

In the past, researchers have attempted to correlate the effect that the visual, vestibular and somatosensory systems have on postural control. One leading method of correlating the effect of these systems on postural control is known as the Romberg test. This test involves the comparison of an individual's quiet-standing postural sway under eyes-open and eyes-closed condition. Since, as with other traditional analyses of stabilograms, the Romberg test analyzes the results of the stabilogram based on, for example, maximum displacement and total distance traversed, the interpretation of the results obtained from the Romberg test has been limited by the inability to obtain repeatable, physiologically meaningful information from stabilograms. Nonetheless, according to the conclusions of the Romberg test, postural instability, as measured by center of pressure summary statistics, generally increases when a subject closes his or her eyes.

Other contemporary scientific and clinical investigations in postural control have directed their attention to analyzing the response of the human body to various external perturbations. Although this reflexive approach enables a clinician to examine the input/output characteristics of different closed-loop feedback systems, it does not consider explicitly the stabilizing roles of possible short term open-loop control schemes or the steady-state behavior of the human body during periods of undisturbed stance. However, since static posturography lacks a reliable, consistently useful approach or technique for extracting repeatable, physiologically meaningful information from stabilograms, a subject's balance is typically analyzed with dynamic posturography, i.e., applying an external force to the subject and monitoring the recovery of balance.

In addition, dynamic posturography, by its very nature, is considerably more hazardous and physically taxing than static posturography, especially in aged and physically infirm subjects. For example, it is much safer to analyze a person who is likely to lose his or her balance on a static force plate and monitor the postural control system at work than it is to apply an external force and then monitor the postural control system as he or she recovers his or her balance. Since, until now, there was no known way to harness the data provided by the stabilogram produced during quiet standing, many stabilogram analyses have been directed to dynamic posturography.

SUMMARY OF THE INVENTION

It is an object of the preferred embodiment to provide a method and an apparatus for processing the center of pressure data on a stabilogram such that physiologically meaningful information is obtained.

It is another object of the preferred embodiment to provide a method and an apparatus for extracting repeatable information from the center of pressure time series.

It is a further object of the preferred embodiment to provide a method and an apparatus for monitoring an open-loop control system operating in the postural control mechanism.

It is a further object of the preferred embodiment to provide a method and an apparatus for monitoring a closed-loop control system operating in the postural control mechanism.

It is a further object of the preferred embodiment to develop a method and an apparatus for monitoring a subject's balance during quiet standing without applying an external perturbation thereto.

It is still another object of the preferred embodiment to provide non-invasive diagnostic and therapeutic procedures for determining the level of postural instability of subjects.

It is a further object of the preferred embodiment to assess the effect on postural stability when a subject's visual input is removed.

These and other objects of the preferred embodiment are accomplished by using statistical mechanics to manipulate the data provided by a traditional stabilogram. More particularly, the data generated by the stabilogram is used to generate a stabilogram diffusion plot. The stabilogram diffusion plot depicts the mean square displacement of the center of pressure vs. the time interval. Since averaged stabilogram diffusion plots are reproducible, they afford a conceptual framework for identifying and characterizing short term open-loop and long term closed-loop dynamics of the human postural control system.

The preferred embodiment relies on the statistical mechanical model known as Brownian motion to generate and interpret the data on the stabilogram diffusion plot. When reduced to a single dimension, Brownian motion describes the random movement of a particle along a straight line. The mean square displacement of a one-dimensional random walk is related to the time interval $\Delta t$ by the expression:

$$<\Delta x^2> = 2D\Delta t \qquad (1)$$

where D is known as the diffusion coefficient. The diffusion coefficient D represents the level of stochastic activity of a particular point. The one dimensional Brownian analysis can easily be extended to two or three dimensions. Since the center of pressure is essentially a point beneath the feet, it can be modeled according to the above diffusion equation.

The data on the stabilogram diffusion plot is generated by having a subject stand on a force platform and then measuring the time varying displacement of the center of pressure beneath his or her feet. The squared distance that the center of pressure travels during a plurality of time intervals is then calculated and averaged over the number of time intervals making up the original stabilogram. The result provides a single point on the stabilogram diffusion plot. The squared distance that the center of pressure travels during a plurality of further different time intervals is then calculated and averaged over the number of these time intervals making up the original stabilogram, again providing another single point on the stabilogram diffusion plot. This process is repeated until the time interval reaches the length of the time record, after which time a plurality of points are generated on the stabilogram diffusion plot.

Since the methodology of producing the stabilogram diffusion plot is derived from Brownian motion, the Brownian parameters can be used to interpret the data on the stabilogram diffusion plot. First, since the Brownian diffusion coefficient D is indicative of the level of stochastic activity of a particular point, the slope of the line on the stabilogram diffusion plot represents the level of stochastic activity of the center of pressure beneath the subject's feet.

In addition, the slope of the log-log plot of the stabilogram diffusion plot indicates the correlation between the past and future step increments making up the experimental stabilogram time series. If the stochastic process is positively correlated, a Brownian particle moving in a particular direction for some $t_o$ will tend on average to continue in the same direction. On the other hand, if the stochastic process is negatively correlated, the Brownian particle moving in a particular direction for some $t_o$ will tend on average to change directions.

Finally, the stabilogram diffusion plots changed slopes after some small $\Delta t$, e.g., one second. Whereas, according to classical Brownian motion, the mean square displacement of a random walk grows linearly with a constant slope for increasing time intervals, the slope of the stabilogram diffusion plot changed after a transition point. This indicates that, in the time before the transition point, a short term open-loop system operates to maintain an upright posture before the long term closed-loop feedback system activates. Then, at the transition point, the postural control system switches from an open-loop to a closed-loop system.

One practical application of the preferred embodiment involves assessing the effect on postural stability when a subject's visual input is removed. In particular, a stabilogram diffusion plot is generated for a subject having his or her eyes open. Then, a stabilogram diffusion plot is generated for a subject having his or her eyes closed. Since the stabilogram diffusion plot is reproducible, any notable difference between the plot generated while the subject has visual input and while the subject is without visual input can be attributed to the physiological contribution that the visual input has on the postural control system.

According to stabilogram diffusion plots generated in accordance with the preferred embodiment, approximately half of the subjects tested demonstrated an improvement in stability when visual input was removed, i.e., the level of stochastic activity of the center of pressure decreased when visual input was removed. These results contradict the previously accepted Romberg theory that postural instability virtually always increases when visual input is removed. It should be noted, though, that the eyes open/eyes closed test is only but one application for the stabilogram diffusion analysis according to the preferred embodiment. Other applications would involve the testing of patients or subjects with reduced proprioceptive or vestibular function.

Since the stabilogram diffusion plot can be reproduced, a multitude of other potential practical applications can employ this information. For example, a database of normative stabilogram diffusion plots could be established, and then elderly or injured patients could be evaluated by comparing their stabilogram diffusion plots with the normative database. Alternatively, a patient's recovery could be monitored based on the improvement of their stabilogram diffusion plots taken at different times during the recovery process. Numerous other applications are possible.

These and other features and objects of the present invention will become apparent when the specification is read in conjunction with the accompanying drawings.

DETAILED DESCRIPTION OF PREFERRED EMBODIMENT

Figure 1:
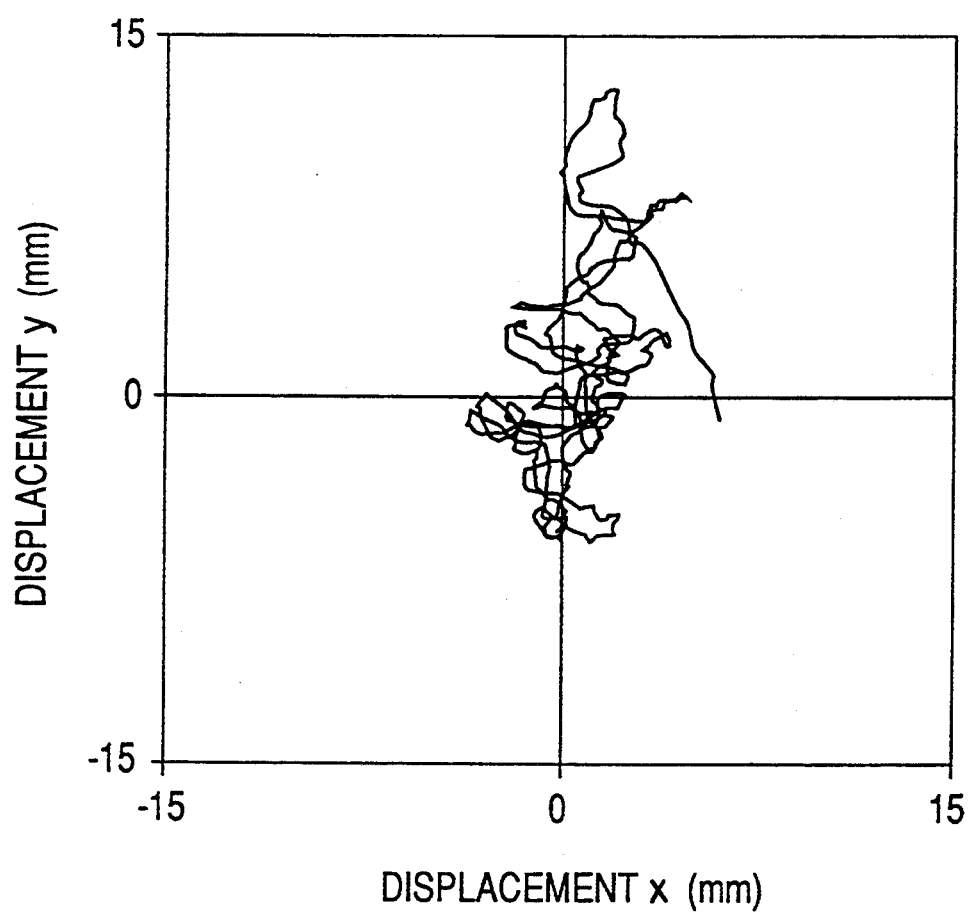
FIG. 1 is a typical thirty second stabilogram for a healthy individual during quiet standing.

According to the preferred embodiment, techniques from statistical mechanics are employed to manipulate the data obtained from the traditional stabilogram. Since the data provided by a traditional stabilogram analysis have generally not yielded repeatable, physiologically meaningful information, the preferred embodiment relies on statistical mechanical techniques to manipulate the data such that repeatable, physiologically meaningful information is obtained. The data from the traditional stabilogram is manipulated with statistical mechanics to generate a stabilogram diffusion plot. The stabilogram diffusion plot depicts the mean square displacement of the center of pressure vs. the time interval. Since stabilogram diffusion plots are reproducible, they afford a conceptual framework for identifying and characterizing short term open-loop and long term closed-loop dynamics of the human postural control system.

Since the center of pressure is a measure of whole body dynamics, it represents the summed effect of a number of different neuromusculoskeletal components acting at a number of different joints. This inherent feature has confounded the majority of previous attempts at interpreting stabilograms from a motor control perspective. An advantage of the stabilogram-diffusion parameters of the preferred embodiment is that they can be directly related to the resultant steady-state behavior and functional interaction of the open-loop and closed-loop neuromuscular mechanisms underlying postural control.

As is well known to those skilled in the art, statistical mechanics is based at least in part on the premise that although the outcome of an individual random event is unpredictable, it is still possible to obtain definite expressions for the probabilities of various aspects of a stochastic process. A classic example of a statistical mechanical phenomenon is Brownian motion. The simplest case of Brownian motion is the random movement of a single particle along a straight line. This construct is known as a one-dimensional random walk.

The mean square displacement $<\Delta x^2>$ of a one-dimensional random walk is related to the time interval $\Delta t$ by the expression:

$$<\Delta x^2> = 2D\Delta t \qquad (1)$$

where D is the diffusion coefficient. The brackets $<\ >$ denote an average over time or an ensemble average over a large number of samples. The diffusion coefficient D represents an average measure of the stochastic activity of a random walker, i.e., it is directly related to its jump frequency and/or amplitude. The mean square displacement $<\Delta x^2>$ is easily extended to higher dimensions, i.e., random walks in a plane or in three-dimensional space. For example, when analyzing the movement of a particle in a plane, the mean square displacement $<\Delta r^2>$ has a first component $<\Delta x^2>$ along the x-axis and a second component $<\Delta y^2>$ along the y-axis. The planar mean square displacement $<\Delta r^2>$ is related to $<\Delta x^2>$ and $<\Delta y^2>$ through the expression wherein $<\Delta r^2> = <\Delta x^2> + <\Delta y^2>$.

Similarly, the diffusion coefficient D can be extended to higher dimensions. For example, for particle movement in a plane, the diffusion coefficient $D_r$ has a first component $D_x$ along the x-axis and a second component $D_y$ along the y-axis. Since $<\Delta r^2> = <\Delta x^2> + <\Delta y^2>$, it follows that the respective planar diffusion coefficients are linear combinations of the diffusion coefficients calculated for the x and y directions, i.e., $D_r = D_x + D_y$.

Since the center of pressure can be reduced to a point, its movement beneath the feet can be modeled according to Brownian motion. In particular, when analyzing the time varying displacement $\Delta r$ of the center of pressure in a plane, there is a mediolateral component $\Delta x$ and an anteroposterior component $\Delta y$ wherein $<\Delta r^2> = <\Delta x^2> + <\Delta y^2>$.

Similarly, the diffusion coefficient $D_r$ of the center of pressure has a mediolateral component $D_x$ and an anteroposterior component $D_y$. Since $<\Delta r^2> = <\Delta x^2> + <\Delta y^2>$, it follows that the respective planar diffusion coefficients are linear combinations of the diffusion coefficients calculated for the x and y directions, i.e., $D_r = D_x + D_y$. When Brownian motion is extended to the center of pressure analysis, the planar diffusion coefficient $D_r$ reflects the level of stochastic activity of the center of pressure about the plane of support. The diffusion coefficient D quantifies postural instability, i.e., a larger diffusion coefficient D corresponds to a less tightly regulated control system.

In addition to classical Brownian motion, the preferred embodiment relies upon a mathematical concept known as fractional Brownian motion, which is also well known to those skilled in the art. For fractional Brownian motion, the relation given by equation (1) is generalized by the following scaling law:

$$<\Delta x^2> \sim \Delta t^{2H} \qquad (2)$$

where the scaling exponent H is any real number in the range $0 < H < 1$. The scaling exponent H quantifies the correlation between the step increments making up an experimental stabilogram time series. For classical Brownian motion, $H = \frac{1}{2}$. As can be seen from equation (2), the scaling exponent H can be determined from the slope of the log-log plot of the mean square displacement vs. $\Delta t$ curve, or in other words, from the slope of the log-log plot of the stabilogram diffusion plot.

An important feature of fractional Brownian motion is that past increments in a particle's displacement are correlated with future increments. The only exception to this rule is the case of $H = \frac{1}{2}$, which corresponds to a classical random walk. For fractional Brownian motion, the correlation function C, which is time independent, is given by the expression, $$C = 2(2^{2H-1} - 1) \qquad (3)$$

For $H > \frac{1}{2}$, the stochastic process is positively correlated, i.e., $C > 0$. In this case, a fractional Brownian particle moving in a particular direction for some $t_0$ will tend to continue in the same direction for $t > t_0$. In general, if there are increasing trends in the past, there will generally be on the average increasing trends in the future. Alternatively, if there are decreasing trends in the past, there will generally be on the average decreasing trends in the future. This type of behavior is know as persistence.

The opposite situation occurs for $H < \frac{1}{2}$, in which case the stochastic process is negatively correlated, i.e., $C < 0$. In this case, if there are increasing trends in the past, there will generally be on the average decreasing trends in the future. Alternatively, if there are decreasing trends in the past, there will generally be on the average increasing trends in the future. This type of behavior is know as antipersistence.

Figure 2:
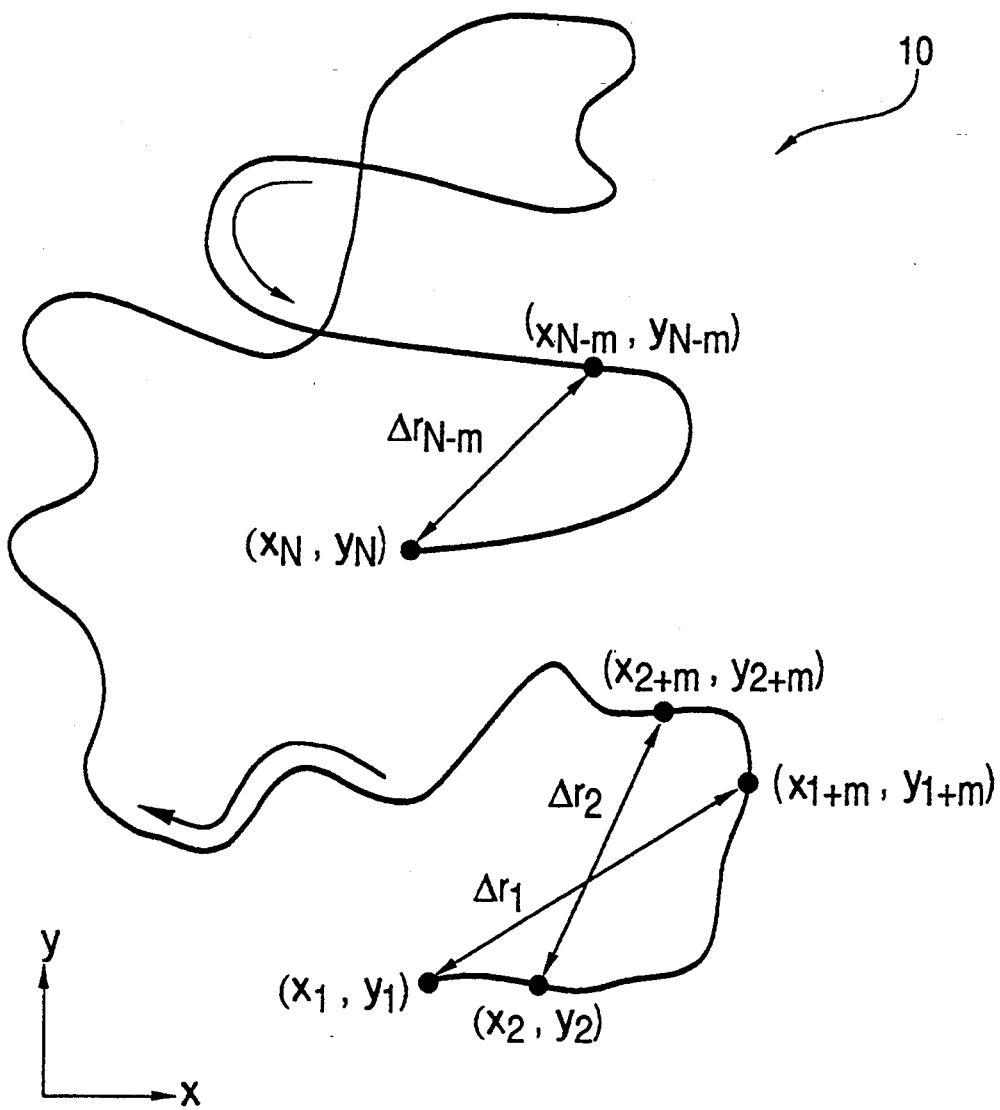
FIG. 2 is a schematic of the movement of the center of pressure during some time period, e.g., 30 seconds.

With these mathematical models, the preferred embodiment synthesizes the center of pressure signature into meaningful parameters which relate to the neuromuscular system effecting postural control. With reference to FIG. 2, there is shown a snapshot of a center of pressure signature 10. The preferred embodiment involves the examination of the quiet-standing center of pressure trajectories as one-dimensional and two-dimensional random walks. To obtain a snapshot of the center of pressure trajectory such as that shown in FIG. 2, a subject stands on a force platform, e.g., a Kistler 9287 multicomponent force platform.

In terms of the center of pressure analysis, equation (1) above, which describes classical Brownian motion, is adapted to the following equation:

$$<\Delta r^2>_{\Delta t} = \frac{\sum_{i=1}^{N-m}(\Delta r_i)^2}{N-m} \quad (4)$$

Wherein m represents a predetermined number of data intervals separated by a predetermined time, $\Delta r^2$ represents the square of the distance traveled by the center of pressure, and $(\Delta r_i)^2$ represents the square of the distance traveled by the center of pressure during a specific time interval. According to equation (4), the displacement analysis is carried out by computing the mean square of the displacements between predetermined pairs of points along the center of pressure snapshot during a specified time interval $\Delta t$. In the center of pressure signature 10 of FIG. 2, point $x_1$, $y_1$ is indicative of the beginning of the time series, while point $x_N$, $y_N$ is indicative of the end of the time series. During the first time interval $\Delta t$ of FIG. 2, the center of pressure moves from point $x_1$, $y_1$ to point $x_{1+m}$, $y_{1+m}$.

Within the time series, the movement of the center of pressure is further broken down, after the expiration of the first time interval $\Delta t_i$, into more time intervals $\Delta t_n$. The first time interval $\Delta t_1$ begins at the point $x_1$, $y_1$ and lasts a predetermined amount of time. The second time interval $\Delta t_2$ begins at the point $x_2$, $y_2$ and lasts the predetermined amount of time.

More specifically, during the first time interval $\Delta t_1$, the center of pressure moved from point $x_1$, $y_1$ to point $x_{1+m}$, $y_{1+m}$ on the force plate. From the Pythagorean Theorem, the square of the distance $\Delta r^2$ between $x_1$, $y_1$ and $x_{1+m}$, $y_{1+m}$ is computed as the sum of $\Delta x^2$ and $\Delta y^2$. During the second time interval $\Delta t_2$, the center of pressure moved from point $x_2$, $y_2$ to point $x_{2+m}$, $y_{2+m}$ on the force plate. From the Pythagorean Theorem, the square of the distance $\Delta r^2$ between $x_2$, $y_2$ and $x_{2+m}$, $y_{2+m}$ is computed as the sum of $\Delta x^2$ and $\Delta y^2$. The displacement of the center of pressure during further time intervals $\Delta_n$ is calculated until the time series expires.

Figure 3:
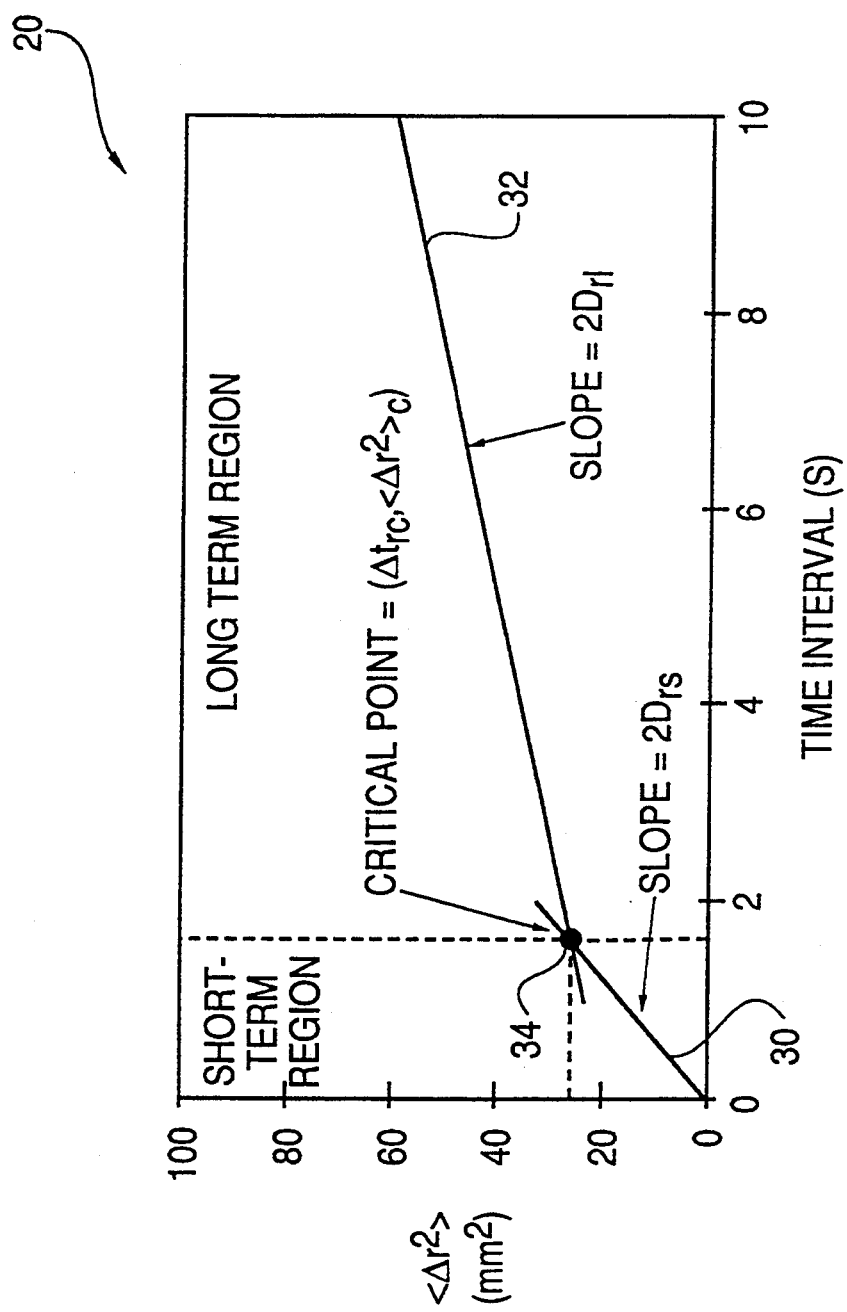
FIG. 3 is a schematic representation of a stabilogram diffusion plot generated according to the method of the preferred embodiment.

An average of the square of the distances $<\Delta r^2>_{\Delta t}$ between pairs of points along the center of pressure trajectory 10 making up the center of pressure time series is obtained from equation (4). The mean square displacement $<\Delta r^2>$ between the pairs of points during the time interval $\Delta t$ is plotted as a single point on the stabilogram diffusion plot (FIG. 3). For example, according to equation (4), the square of the distances between the pairs of points, e.g., $x_1$, $y_1$ and $x_{1+m}$, $y_{1+m}$, etc., separated in time by a specified time interval $\Delta t$ are added and then averaged over the number of time intervals $\Delta t_1$ to $\Delta t_{N-m}$ comprising the time series. When the mean square displacement for the time interval $\Delta t$ is obtained, the result is plotted as a single point on the stabilogram diffusion plot (FIG. 3).

This process is repeated for increasing values of $\Delta t$. Accordingly, the stabilogram diffusion plot represents a compilation of data obtained from a plurality of time intervals $\Delta t$ in which center of pressure signatures, one of which is shown in FIG. 2, are analyzed according to equation (4). After a predetermined amount of time, e.g., a time interval of 10 seconds, a plurality of data points and a stabilogram diffusion plot are obtained.

A typical stabilogram diffusion plot 20 is shown in FIG. 3. In virtually all of the subjects tested, the stabilogram diffusion plot had a line 30 with a first slope and a line 32 with a second slope. The slope of the first line 30 was generally greater than the slope of the second line 32. A transition or critical point 34 generally marks the transition from the first line 30 to the second line 32. At least three sets of physiologically meaningful parameters are gleaned from the stabilogram diffusion plot: the transition point, the diffusion coefficients D and the scaling exponents H.

The transition point occurred in all of the subjects analyzed. For ordinary Brownian motion, the mean square displacement of a random walk grows linearly with a constant slope for an increasing time interval, e.g., equation (1). The stabilogram diffusion plots, on the other hand, changed slope after a transition or critical point 34 at some small $\Delta t$. Transition point 34 indicates that, in addition to known closed-loop feedback control mechanisms, the postural control system also employs open-loop control schemes, the output of which may take the form of descending commands to different postural muscles.

Since skeletal muscles are incapable of producing purely constant forces, the open-loop activation signals result in small mechanical fluctuations at various joints of the body. The fluctuations and their associated drift effects are left unchecked by the postural control system until they exceed some systematic threshold value, after which corrective closed-loop feedback mechanisms are called into play. The transition point quantifies the spatial and temporal characteristics of this switching phenomenon. The transition point generally occurred for healthy, young subjects at a short time interval, e.g., one second.

In addition to the transition point 34, the stabilogram diffusion plot yields two diffusion coefficients D and two scaling exponents H. Since the slope of the line 30 changes at transition point 34, the center of pressure first behaves according to a short term diffusion coefficient $D_s$ and a short term scaling exponent $H_s$ corresponding to the time in which the control system is defined by line 30. Similarly, beyond the transition point 34, the center of pressure then behaves according to a long term diffusion coefficient $D_l$ and a long term scaling exponent $H_l$ corresponding to the time in which the control system is defined by line 32.

First, as to the diffusion coefficient D, since equation (4), which is used to generate the stabilogram diffusion plot of FIG. 3, is derived from the equation defining Brownian motion, e.g., equation (1) above, the slopes of the lines 30, 32 on the resulting stabilogram diffusion plot of FIG. 3 are proportional to the Brownian diffusion coefficient D. The diffusion coefficients D are obtained from the slopes of the resultant linear-linear plots of lines 30, 32. For example, as is well known to one skilled in the art, the slope of lines 30, 32 could be obtained by utilizing the method of least squares to fit straight lines through defined portions of the stabilogram diffusion plot.

As previously discussed, the diffusion coefficients D are a significant feature of Brownian motion since they reflect the level of stochastic activity of the analyzed point, the point here being the center of pressure. Therefore, the diffusion coefficients D of the stabilogram diffusion plots indicate the level of stochastic activity of the center of pressure along the mediolateral and anteroposterior axis or about the plane of support. These measurements can thus be used to quantify postural instability, i.e., larger diffusion coefficients D correspond to a less tightly regulated control system and vice versa. More particularly, the short term and long term diffusion coefficients $D_s$, $D_l$ characterize the stochastic activity of the open-loop and closed-loop postural control mechanisms, respectively.

Next, the scaling exponent H can be determined from the slope of the resulting log-log stabilogram diffusion trials. Several statistics are noteworthy from the diffusion coefficient calculations obtained from the trials. First, the short term diffusion coefficients were much greater than the respective long term diffusion coefficients, $D_{js} > D_{jl}$ where $j = x, y, r$. In addition, for the majority of the subjects, the anteroposterior diffusion coefficients were greater than their mediolateral counterparts, i.e., $D_{yi} > D_{xi}$ where $i = s, l$. This result was not unexpected since the anteroposterior postural sway is typically greater than the mediolateral sway. This asymmetry can be attributed largely to the geometry of the lower limb. In particular, the ankle or tibiotarsal joint is, for example, mainly a simple hinge joint which allows rotations (plantarflexion/dorsiflexion) in the sagittal plane. Thus, from a passive mechanical standpoint, upright bipedal stance is considerably more stable in the frontal plane than in the sagittal plane. Finally, since $<\Delta r^2> = <\Delta x^2> + <\Delta y^2>$, it follows that the respective planar diffusion coefficients are linear combinations of the diffusion coefficients calculated for the x and y directions, i.e., $D_{ri} = D_{xi} + D_{yi}$.

TABLE I

| | Diffusion Coefficients ($mm^{2s-1}$): Mean ± Standard Deviation | | | | | |
|---|---|---|---|---|---|---|
| | Mediolateral (x) | | Anteroposterior (y) | | Planar (r) | |
| Subj. | $D_{xs}$ | $D_{xl}$ | $D_{ys}$ | $D_{yl}$ | $D_{rs}$ | $D_{rl}$ |
| 1 | 3.23 ± 0.52 | 0.60 ± 0.28 | 5.05 ± 0.25 | 1.37 ± 0.07 | 8.28 ± 0.74 | 1.97 ± 0.23 |
| 2 | 2.33 ± 0.16 | 0.24 ± 0.07 | 4.10 ± 0.62 | 0.55 ± 0.49 | 6.43 ± 0.53 | 0.79 ± 0.45 |
| 3 | 3.35 ± 0.22 | 0.32 ± 0.14 | 6.10 ± 0.86 | 1.13 ± 0.53 | 9.45 ± 0.67 | 1.45 ± 0.57 |
| 4 | 2.91 ± 0.54 | 0.64 ± 0.05 | 4.06 ± 0.19 | 1.09 ± 0.25 | 6.97 ± 0.47 | 1.73 ± 0.21 |
| 5 | 3.47 ± 0.49 | 0.31 ± 0.08 | 3.16 ± 0.58 | 1.02 ± 0.15 | 6.62 ± 0.70 | 1.32 ± 0.13 |
| 6 | 4.31 ± 0.33 | 0.19 ± 0.14 | 7.26 ± 1.84 | 1.00 ± 0.30 | 11.57 ± 2.06 | 1.19 ± 0.33 |
| 7 | 2.89 ± 0.44 | 0.96 ± 0.63 | 2.72 ± 0.29 | 1.11 ± 0.12 | 5.60 ± 0.73 | 2.06 ± 0.57 |
| 8 | 1.20 ± 0.23 | 0.21 ± 0.14 | 2.46 ± 0.41 | 0.45 ± 0.11 | 3.66 ± 0.32 | 0.66 ± 0.03 |
| 9 | 2.53 ± 0.21 | 0.80 ± 0.38 | 4.08 ± 0.53 | 1.47 ± 0.38 | 6.61 ± 0.65 | 2.27 ± 0.29 |
| 10 | 0.58 ± 0.16 | 0.13 ± 0.04 | 1.63 ± 0.11 | 1.06 ± 0.25 | 2.21 ± 0.26 | 1.19 ± 0.22 |
| GM ± SD | 2.68 ± 1.10 | 0.44 ± 0.35 | 4.06 ± 1.76 | 1.02 ± 0.40 | 6.74 ± 2.68 | 1.46 ± 0.59 |

Diffusion coefficients: means and standard deviations for the population of subjects (N = 10). Group means (GM) and standard deviations (SD) for the respective parameters are given in the last row.

plot. As previously discussed, the scaling exponent H quantifies the correlation between the step increments making up an experimental stabilogram time series. As with the diffusion coefficients $D_x$, $D_y$, the scaling exponent H can be calculated for the x and y directions.

In a posturographic investigation, it would be impractical to have subjects stand on a force platform for extended periods of time. Physiological factors such as fatigue would tend to obscure the results. In one of the studies conducted according to the preferred embodiment, a large number of 30 sec. trials for each subject were performed. Each subject was instructed to stand in an upright posture in a standardized stance on the platform. In the standardized stance, the subject's feet were abducted 10° and their heels were separated mediolaterally by a distance of 3 cm. During the testing, the subjects stood barefoot with their arms comfortably at their sides. Each trial lasted for a period of 30 sec. and the force platform data were sampled at a frequency of 100 Hz. A series of thirty trials were conducted for each subject with his eyes open. During these tests, the subjects were instructed to fix their eyes on a point in front of them. Stabilogram diffusion plots were computed for each 30 sec. trial and after ten stabilogram diffusion plots were obtained, they were averaged to obtain a resultant stabilogram diffusion plot for a particular subject. Three resultant plots were thus generated for a subject who participated in thirty trials.

Table I below lists resultant diffusion coefficients D for ten subjects who each participated in thirty 30 sec.

With particular reference to Subject 6 in Table I, very small long term mediolateral diffusion coefficients were calculated. This means that the center of pressure had fully explored the characteristic space for mediolateral sway during the early stages of the long term region of the stabilogram diffusion plot. In other words, after some small Δt, the center of pressure no longer moved any farther away along the x-axis, on the average, from some relative point. Under these conditions, the center of pressure trajectory saturated to some boundary value. As to the anteroposterior sway of Subject 6, however, the stabilogram did not saturate to a boundary value during the observed time interval.

Table II below lists resultant scaling exponents H for the same ten subjects of Table I. As to the scaling exponents H, it is noteworthy that the short term regions for the ten subjects generally produced short term scaling exponents $H_{js}$ much greater than 0.5. Thus, over the short term intervals during quiet standing, the center of pressure trajectory behaved as a positively correlated random walk, i.e., one which tends to move away from some relative equilibrium point following an external perturbation (indicative of open-loop control). On the other hand, the long term scaling exponents $H_{jl}$ were generally much less than 0.5. Thus, over the long term intervals during quiet standing, the center of pressure trajectory behaved as a negatively correlated random walk, i.e., one which tends to return to a relative equilibrium point following a perturbation (indicative of closed-loop control).

ated for a subject having his or her eyes closed. Since the stabilogram diffusion plot is reproducible, any nota-

TABLE II

Scaling Exponents: Mean ± Standard Deviation

| Subj. | Mediolateral (x) | | Anteroposterior (y) | | Planar (r) | |
|---|---|---|---|---|---|---|
| | $H_{xs}$ | $H_{xl}$ | $H_{ys}$ | $H_{yl}$ | $H_{rs}$ | $H_{rl}$ |
| 1 | 0.71 ± 0.02 | 0.26 ± 0.05 | 0.73 ± 0.01 | 0.39 ± 0.05 | 0.72 ± 0.01 | 0.35 ± 0.03 |
| 2 | 0.74 ± 0.02 | 0.18 ± 0.02 | 0.81 ± 0.03 | 0.17 ± 0.10 | 0.78 ± 0.03 | 0.17 ± 0.07 |
| 3 | 0.76 ± 0.01 | 0.18 ± 0.02 | 0.78 ± 0.02 | 0.34 ± 0.08 | 0.77 ± 0.01 | 0.28 ± 0.06 |
| 4 | 0.78 ± 0.03 | 0.31 ± 0.05 | 0.79 ± 0.01 | 0.30 ± 0.07 | 0.79 ± 0.02 | 0.31 ± 0.06 |
| 5 | 0.78 ± 0.01 | 0.11 ± 0.05 | 0.76 ± 0.03 | 0.31 ± 0.01 | 0.77 ± 0.01 | 0.24 ± 0.02 |
| 6 | 0.79 ± 0.01 | 0.06 ± 0.04 | 0.85 ± 0.02 | 0.17 ± 0.04 | 0.82 ± 0.02 | 0.14 ± 0.03 |
| 7 | 0.77 ± 0.01 | 0.27 ± 0.10 | 0.79 ± 0.01 | 0.34 ± 0.02 | 0.78 ± 0.01 | 0.31 ± 0.04 |
| 8 | 0.65 ± 0.02 | 0.21 ± 0.11 | 0.71 ± 0.03 | 0.24 ± 0.05 | 0.69 ± 0.02 | 0.23 ± 0.01 |
| 9 | 0.73 ± 0.03 | 0.29 ± 0.07 | 0.79 ± 0.03 | 0.37 ± 0.08 | 0.76 ± 0.03 | 0.34 ± 0.03 |
| 10 | 0.57 ± 0.03 | 0.26 ± 0.05 | 0.72 ± 0.02 | 0.53 ± 0.05 | 0.68 ± 0.01 | 0.47 ± 0.04 |
| GM ± SD | 0.73 ± 0.07 | 0.21 ± 0.10 | 0.77 ± 0.05 | 0.31 ± 0.12 | 0.76 ± 0.05 | 0.28 ± 0.10 |

Scaling exponents: means and standard deviations for the population of subjects (N = 10). Group means (GM) and standard deviations (SD) for the respective parameters are given in the last row.

Table III below lists transition or critical point coordinates for the same ten subjects of Tables I and II. The transition point coordinates are indicative of heretofore unknown neuromuscular control systems at work. From an analytical standpoint, these coordinates approximate the transition point at which the slope of a resultant stabilogram diffusion plot changes considerably. From a physiological standpoint, however, these coordinates represent the point at which the postural control system switches over from open-loop control to closed-loop control. By analyzing stabilograms as fractional Brownian motion, it was revealed that at least two distinctly different neuromuscular control mechanisms, one which exhibits persistence and another which exhibits antipersistence, are functioning during quiet standing. More specifically, these results indicate that over short term intervals, open-loop control systems are used by the postural control system whereas over long term intervals, closed-loop control schemes are called into play.

ble difference between the plot generated while the subject has visual input and the plot generated while the subject is without visual input can be attributed to the physiological contribution of the visual input to the postural control system.

For roughly half of a group of subjects tested in a second study, postural stability generally diminished when visual input was removed, i.e., the level of stochastic activity of the center of pressure increased when the subject was blindfolded. These results tend to support the basic premise of the Romberg theory insofar as postural stability decreased when the visual input was removed. However, for roughly the other half of the subjects tested, postural stability improved when visual input was removed, i.e., the level of stochastic activity of the center of pressure decreased when the subject was blindfolded. These results, in distinction with the results from the first set of subjects, directly undermine the conclusions of the Romberg theory that postural stability virtually always decreases when visual input is

TABLE III

Critical Point Coordinates:
Time Intervals (s) and Mean Square Displacements (mm$^2$)
Mean ± Standard Deviation

| Subj. | Mediolateral (x) | | Anteroposterior (y) | | Planar (r) | |
|---|---|---|---|---|---|---|
| | $\Delta t_{xe}$ | $<\Delta x^2>e$ | $\Delta t_{ye}$ | $<\Delta y^2>c$ | $\Delta t_{re}$ | $<\Delta r^2>_e$ |
| 1 | 0.98 ± 0.27 | 5.38 ± 1.01 | 0.42 ± 0.32 | 3.67 ± 2.93 | 0.61 ± 0.28 | 9.26 ± 3.57 |
| 2 | 1.20 ± 0.16 | 5.28 ± 0.40 | 1.67 ± 0.15 | 12.85 ± 1.99 | 1.50 ± 0.10 | 18.15 ± 2.25 |
| 3 | 0.87 ± 0.17 | 5.44 ± 1.49 | 0.33 ± 0.15 | 3.55 ± 2.14 | 0.55 ± 0.88 | 9.34 ± 1.22 |
| 4 | 0.81 ± 0.14 | 4.15 ± 1.02 | 1.28 ± 0.67 | 9.68 ± 5.02 | 1.06 ± 0.33 | 13.80 ± 5.70 |
| 5 | 0.83 ± 0.08 | 5.32 ± 1.02 | 1.57 ± 0.54 | 9.57 ± 4.21 | 1.15 ± 0.27 | 14.28 ± 3.14 |
| 6 | 1.30 ± 0.16 | 10.48 ± 2.15 | 1.36 ± 0.19 | 18.86 ± 3.37 | 1.33 ± 0.05 | 29.37 ± 5.04 |
| 7 | 1.25 ± 0.36 | 7.15 ± 1.62 | 1.21 ± 0.54 | 6.68 ± 2.37 | 1.23 ± 0.40 | 13.90 ± 3.45 |
| 8 | 1.23 ± 0.31 | 2.94 ± 1.24 | 1.35 ± 0.21 | 6.51 ± 2.03 | 1.35 ± 0.10 | 9.46 ± 1.53 |
| 9 | 1.10 ± 0.68 | 5.65 ± 3.24 | 1.00 ± 0.25 | 7.22 ± 0.97 | 0.85 ± 0.26 | 11.03 ± 3.76 |
| 10 | 1.04 ± 0.39 | 1.10 ± 0.26 | 0.56 ± 0.18 | 1.58 ± 0.39 | 0.72 ± 0.23 | 2.80 ± 0.64 |
| GM ± SD | 1.05 ± 0.32 | 5.28 ± 2.73 | 1.07 ± 0.55 | 8.02 ± 5.44 | 1.04 ± 0.38 | 13.14 ± 7.34 |

Critical point coordinates (time intervals and mean square displacements): means and standard deviations for the population of subjects (N = 10). Group means (GM) and standard deviation (SD) for the respective parameters are given in the last row.

With the analytical technique of the preferred embodiment, repeatable, physiologically meaningful information can be extracted from the center of pressure signature during quiet standing.

One practical application of the preferred embodiment relies on the stabilogram diffusion plot to assess the effect on postural stability when visual input is removed from the subject. In particular, a stabilogram diffusion plot is generated for a subject having his or her eyes open. Then, a stabilogram diffusion plot is generremoved. Testing the validity of previously accepted postural theories, e.g., the Romberg theory, is but one practical application for the preferred embodiment.

In addition, the preferred embodiment can be used as a non-invasive scientific tool for characterizing quantitatively the performance of the human postural control system. By way of example, and without intending to limit the preferred embodiment, the analytical technique used therein has numerous other potential practical, scientific and research applications. For example, a normative database of stabilogram diffusion plots could be established, and from that database comparisons could be made between the plots in the database and the stabilogram diffusion plot of a particular subject. These comparisons could be used to assess the degree of postural stability changes resulting from injury, disease and the aging process.

Alternatively, the technique could be used in rehabilitation protocols. For example, if the subject contracted a disease or was injured, the rate of recovery could be monitored by creating a stabilogram diffusion plot at a first time, and comparing it with a stabilogram diffusion plot of the same individual taken at another later time. During a course of therapy, the diffusion plot of the individual will indicate, based on the diffusion coefficients D, scaling exponents H and critical points, whether improvement in balance has occurred during the time between the measurement of the first and second stabilogram diffusion plots.

Still further, the technique can serve as a foundation for biofeedback techniques and methodologies. Here, the subject would stand on the force plate and, if, for example, the anteroposterior sway exhibited a large diffusion coefficient D, which indicates a loosely regulated system, the subject would attempt to correct the instability by altering the anteroposterior sway. Such biofeedback applications would seek to improve an individual's balance and stability.

Alternatively, the preferred embodiment could be utilized by prosthetic designers to gauge the influence of competing prosthetic designs on postural stability.

Still further, it is contemplated that the invention could be used to assess the effect that various drugs have on an individual's balance. For example, a control group could be given a placebo while a study group could be given a particular drug under investigation. A force plate analysis of each subject would be conducted to generate a stabilogram diffusion plot. The results between the control group and the study group would then be compared for differences in the stabilogram diffusion plots. Any notable differences between the stabilogram diffusion plots of the control group and the stabilogram diffusion plots of the study group could then be attributed to the effect that the drug had on the study group.

Still further, the preferred embodiment could be employed by neurology departments of hospitals, geriatric departments and programs, retirement homes and communities, preventive care hospitals and medical centers, rehabilitation hospitals, international space programs, industries with workers who are at risk of experiencing fall-related injuries, insurance companies, biomedical-engineering research and teaching programs, physical therapy research and teaching programs, medical schools, state and local police departments (e.g., sobriety check points), athletic programs, exercise/fitness centers and athletic shoe companies.

Figure 4:
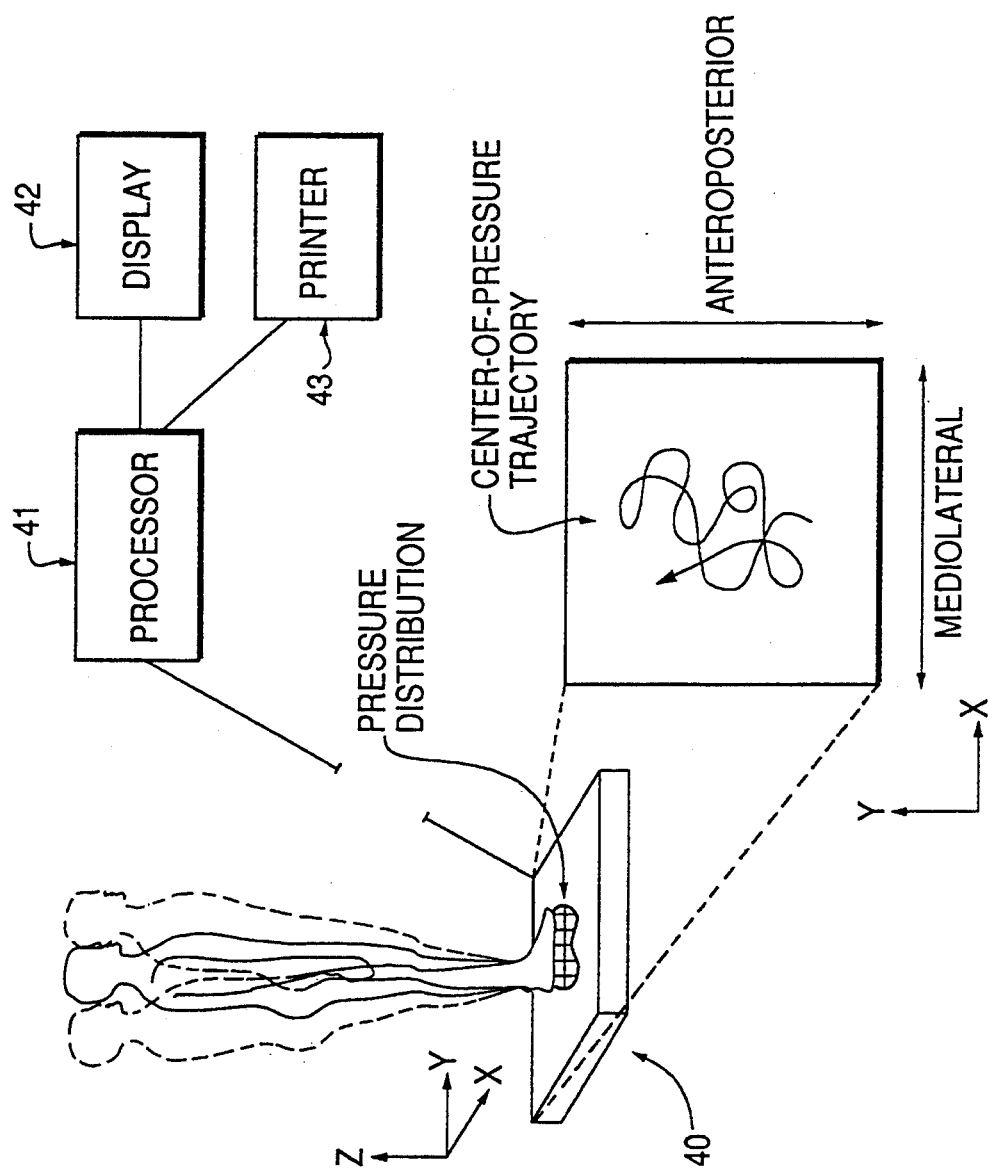
FIG. 4 is a block diagram of an apparatus according to one embodiment of the present invention.

As shown in FIG. 4, an apparatus for measuring and analyzing the human postural control system comprises a force plate (40) containing a set of sensors which respond to pressure. Pressure sensitive sensors are well known to those of ordinary skill in the art. Data from the sensors is transferred to a processor (41) which presents it for viewing by the user for a display (42), such as a monitor, or a printer (43). The processor also stores the data and compiles and contrasts it with a normative database of stored information or individual data obtained from earlier evaluations of the subject. The operation performed by the processor is described more fully above in connection with the method of implementing various aspects of the invention.

Thus, as demonstrated, the preferred embodiment could be incorporated into a multitude of applications in which the balance of a subject is of concern.

In addition, while the preferred embodiment has been described with reference to static measurements of the center of pressure, it is within the purview of the preferred embodiment to extend the analysis to dynamic posturographic protocols. For example, a subject would be placed on a force platform, and an external perturbation would be applied thereto. Using techniques and theoretical concepts from statistical mechanics, such as fluctuation-dissipation theory, the preferred embodiment would analyze the dynamics of how the center of pressure returns to a relative equilibrium point following an external disturbance. Such an analysis could yield further useful information about the operational characteristics and functional interaction of the open-loop and close-loop postural control mechanisms.

The present invention has been described with reference to the preferred embodiment. This embodiment, however, is merely for example only and the present invention is not intended to be restricted thereto. It will be understood by those skilled in the art that variations and modifications can be easily made within the scope of the present invention as defined by the appended claims.

We claim:

1. A method for analyzing the movement of the center of pressure beneath a subject's feet comprising the steps of:
    a. providing a force plate having a plurality of pressure sensors;
    b. positioning the subject on said force plate;
    c. utilizing said pressure sensors to generate signals indicative of the pressure applied by said subject's feet;
    d. storing data representing the movement of the center of pressure beneath the subject's feet by using said signals; and
    e. generating, by statistical mechanical models, a stabilogram diffusion plot describing the movement of the center of pressure.

2. The method according to claim 1, further comprising the step of comparing the generated plot with plots in a normative database to determine whether differences exist between the generated plot and the plots in the normative database.

3. The method according to claim 1, wherein step c. further comprises the step of calculating the mean square displacement of the center of pressure for a plurality of predetermined time intervals.

4. The method according to claim 3, further comprising the step of plotting the mean square displacement of the center of pressure versus a plurality of said predetermined time intervals.

5. The method according to claim 1, further comprising the step of employing the statistical mechanical model of Brownian motion to describe the movement of the center of pressure.

6. The method according to claim 5, further comprising the step of calculating the mean square displacement of the center of pressure during a first time interval according to the equation $$<\Delta r^2>_{\Delta t} = \frac{\sum_{i=1}^{N-m} (\Delta r_i)^2}{N - m} \quad (4)$$

wherein:
m represents a predetermined number of data intervals separated by a predetermined time;
$(\Delta r_i)^2$ represents the square of the distance traveled by the center of pressure during the time interval; and
N represents the total number of data intervals.

7. The method according to claim 6, further comprising the step of plotting the mean square displacement of the center of pressure during said first time interval as a point on said plot.

8. The method according to claim 7, further comprising the steps of calculating, using equation (4), the mean square displacement of the center of pressure for a plurality of further time intervals and plotting the results of said calculations versus the time interval.

9. The method according to claim 8, further comprising the step of comparing said generated plot with plots in a normative database to determine whether differences exist between the generated plot and the plots in the normative database.

10. The method according to claim 1, wherein said stabilogram diffusion plot is used to diagnose an amount of postural instability in the subject.

11. The method according to claim 1, wherein said plot has at least a first slope, said slope of said plot indicating a level of stochastic activity of the center of pressure.

12. The method according to claim 1, wherein said plot has at least a first slope, said first slope of said plot indicating a tendency of the center of pressure to move away from a first equilibrium point.

13. The method according to claim 12, wherein said plot has a second slope, said second slope of said plot indicating a tendency of the center of pressure to move toward a second equilibrium point.

14. The method according to claim 13, wherein the first slope and the second slope intersect defining a critical point which is characteristic of the subject being analyzed.

15. The method according to claim 1, further comprising the step of removing the subject's visual input by having the subject close his or her eyes and/or by blindfolding the subject.

16. The method according to claim 1, further comprising the step of directing the subject to stand on said force plate with his or her eyes open thereby maintaining the subject's visual input.

17. The method of claim 1 further comprising the steps of:
repeating steps b–d wherein said subject assumed a different posture; and
training said subject a posture to minimize said movement of the center of pressure through comparison of plots from various postures.

18. A method of analyzing the movement of the center of pressure beneath a subject's feet comprising the steps of:
a. providing a force plate having a plurality of pressure sensors;
b. positioning the subject on said force plate during a first session;
c. utilizing said pressure sensors to generate a first set of signals indicative of the amount of pressure applied by said subject's feet;
d. storing data representing the movement of the center of pressure beneath the subject's feet during the first session by using said first set of signals;
e. generating, by statistical mechanical models, a first characteristic plot describing the movement of the center of pressure during the first session;
f. positioning the subject on the force plate during a second session;
g. utilizing said pressure sensors to generate a second set of signals indicative of the amount of pressure applied by said subject's feet;
h. storing data representing the movement of the center of pressure beneath the subject's feet during the second session by using said second set of signals;
i. generating, by the statistical mechanical models, a second characteristic plot describing the movement of the center of pressure during the second session; and
j. comparing the first and second plots to determine whether differences exist therebetween.

19. The method according to claim 18, said plots comprising stabilogram diffusion plots.

20. The method according to claim 19, wherein said stabilogram diffusion plots are used to study the difference in balance of a subject between the first session and the second session.

21. The method according to claim 18, further comprising the step of employing the statistical mechanical model of Brownian motion to describe the movement of the center of pressure.

22. The method according to claim 21, further comprising the step of calculating the mean square displacement of the center of pressure during a first time interval according to the equation $$<\Delta r^2>_{\Delta t} = \frac{\sum_{i=1}^{N-m} (\Delta r_i)^2}{N - m} \quad (4)$$

wherein:
m represents a predetermined number of data intervals separated by a predetermined time;
$(\Delta r_i)^2$ represents the square of the distance traveled by the center of pressure during the time interval; and
N represents the total number of data intervals.

23. The method according to claim 22, further comprising the step of plotting the mean square displacement of the center of pressure during said first time interval as a point on said plot.

24. The method according to claim 23, further comprising the steps of calculating, using equation (4), the mean square displacement of the center of pressure for a plurality of further time intervals and plotting the results of said calculations versus the time interval.

25. The method according to claim 18, further comprising the step of removing the subject's visual input by having the subject close his or her eyes and/or by blindfolding the subject.

26. The method according to claim 18, further comprising the step of directing the subject to stand on said force plate with his or her eyes open thereby maintaining the subject's visual input.

27. A method of analyzing a subject's postural stability as described by the movement of the center of pressure beneath the subject's feet, said method comprising the steps of:
 a. providing a force plate having a plurality of pressure sensors;
 b. collecting data from said pressure sensors on said force plate indicative of the time varying movement of the center of pressure beneath the feet of the subject;
 c. plotting the mean square displacement of the center of pressure versus a predetermined time interval;
 d. calculating the slope of the line representing the mean square displacement of the center of pressure versus the time interval; and
 e. comparing the slope of said line with slopes taken from a normative database.

28. The method according to claim 27, wherein the subject's postural stability is separately analyzed in plurality of sessions before, during and/or after a course of therapy.

29. The method of claim 27 wherein said normative database includes slopes from said subject having a prosthetic limb, each entry in said normative database corresponding to results taken from said subject having a different competing prosthetic design, wherein said subject has yet another competing prosthetic design, and further comprising the step of selecting a prosthetic design for said subject based upon said comparing step.

30. A method of analyzing postural stability of a subject comprising the steps of:
 a. providing a force plate having a plurality of pressure sensors thereon;
 b. placing a person on said force plate wherein said person's feet are both placed upon said force plate and wherein said sensors detect pressure exerted by said persons's feet upon said force plate;
 c. determining the coordinate locations of the center of pressure beneath said person's feet during a first time interval using data collected from said sensors;
 d. determining the square of the distance between pairs of the plurality of coordinate locations;
 e. plotting a point corresponding to the average of said square of the distances versus the time interval; and
 f. repeating steps c. through e. for at least a second time interval to obtain a plurality of plotted points.

31. The method according to claim 30, wherein the subject's postural stability is separately analyzed in a plurality of sessions before, during, and/or after a course of therapy.

32. An apparatus for analyzing the movement of the center of pressure beneath the feet of a subject wherein said subject is positioned on a force plate, said apparatus comprising:
 a. a force plate for providing data representing the movement of the center of pressure beneath the subject's feet;
 b. means for storing said data; and
 c. generating means responsive to said force plate for generating a stabilogram diffusion plot describing the movement of the center of pressure.

33. The apparatus according to claim 32, wherein said generating means comprises means for comparing said characteristic plot with one or more stored plots to determine whether differences exist between said characteristic plot and the one or more stored plots.

34. The apparatus according to claim 33, wherein said generating means further comprises a means for calculating the mean square displacement of the center of pressure for a plurality of predetermined time intervals.

35. The apparatus according to claim 34, further comprising means for plotting the mean square displacement of the center of pressure for a plurality of said predetermined time intervals.

36. The apparatus according to claim 34, wherein said generating means further comprises means for calculating a mean square displacement of the center of pressure during at least a first time interval according to the equation $$<\Delta r^2>_{\Delta t} = \frac{\sum_{i=1}^{N-m}(\Delta r_i)^2}{N-m}$$

wherein:
 m represents a predetermined number of data intervals separated by a predetermined time;
 $(\Delta r_i)^2$ represents the square of the distance traveled by the center of pressure during the time interval; and
 N represents the total number of data intervals.

37. The apparatus according to claim 36, wherein said generating means further comprises means for comparing said characteristic plot with one or more stored plots to determine whether differences exist between the generated plot and the one or more stored plots.

38. An apparatus for analyzing the postural stability of a subject based on the movement of the center of pressure beneath the feet of the subject, comprising:
 a force plate for providing data indicative of the time varying movement of the center of pressure beneath the feet of the subject;
 means for plotting the means square displacement of the center of pressure versus a predetermined time interval;
 means for calculating the slope of a line representing the means square displacement of the center of pressure versus the time interval; and
 means for comparing the slope of said line with at least one stored slope.

39. An apparatus for analyzing the movement of the center of pressure of the feet of a subject comprising:
 a force plate having a plurality of sensors for receiving the feet of said subject and for producing data representing pressure applied by said subject to said force plate;
 a processor for receiving said force plate data, compiling said data, determining information regarding the movement of the center of pressure of the feet of said subject and comparing said determined information with determined information from a normative database; and
 a display for displaying the results of said processor.

* * * * *